(12) United States Patent
Ahoniemi et al.

(10) Patent No.: US 11,207,441 B2
(45) Date of Patent: Dec. 28, 2021

(54) FIBROUS STRUCTURE EXHIBITING AN ANTIMICROBIAL EFFECT

(71) Applicant: ESSITY HYGIENE AND HEALTH AKTIEBOLAG, Gothenburg (SE)

(72) Inventors: Hannu Ahoniemi, Gothenburg (SE); Lars Fingal, Gothenburg (SE); Ulrika Husmark, Gothenburg (SE); Kent Malmgren, Sundsvall (SE); Anna Nihlstrand, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 861 days.

(21) Appl. No.: 15/777,306

(22) PCT Filed: Nov. 20, 2015

(86) PCT No.: PCT/SE2015/051251
§ 371 (c)(1),
(2) Date: May 18, 2018

(87) PCT Pub. No.: WO2017/086850
PCT Pub. Date: May 26, 2017

(65) Prior Publication Data
US 2020/0254135 A1 Aug. 13, 2020

(51) Int. Cl.
*A61L 15/46* (2006.01)
*A61L 15/18* (2006.01)
*A61L 15/42* (2006.01)

(52) U.S. Cl.
CPC .............. *A61L 15/18* (2013.01); *A61L 15/425* (2013.01); *A61L 15/46* (2013.01)

(58) Field of Classification Search
CPC ........ A61F 13/8405; A61F 2013/15463; A61F 2013/15471; A61F 2013/51047; A61F 2013/5109; A61F 2013/530708; A61F 2013/530715; A61F 2013/530737; A61F 2013/8414; A61F 2013/8426; A61L 15/18; A61L 15/46
See application file for complete search history.

(56) References Cited

U.S. PATENT DOCUMENTS

| 2003/0124171 A1 | 7/2003 | Sun et al. |
| 2005/0159063 A1* | 7/2005 | Hill .................... D04H 1/43835 442/327 |
| 2007/0010153 A1 | 1/2007 | Shaffer et al. |

(Continued)

FOREIGN PATENT DOCUMENTS

| CN | 1631308 A | 6/2005 |
| CN | 104027279 A | 9/2014 |

(Continued)

OTHER PUBLICATIONS

Russian Office Action dated Apr. 10, 2019 issued in Russian patent application No. 2018122205 (5 pages) and its English-language translation thereof (7 pages).

(Continued)

*Primary Examiner* — Catharine L Anderson
(74) *Attorney, Agent, or Firm* — Buchanan Ingersoll & Rooney PC

(57) ABSTRACT

A fibrous structure exhibits an absorbency time of equal to or less than 1.5 s and exhibits an antimicrobial effect.

14 Claims, 1 Drawing Sheet

(56) References Cited

U.S. PATENT DOCUMENTS

| | | |
|---|---|---|
| 2007/0270071 A1 | 11/2007 | Greer et al. |
| 2007/0275043 A1 | 11/2007 | Freeman et al. |
| 2010/0086511 A1 | 4/2010 | Sakamoto |
| 2010/0286641 A1 | 11/2010 | Yao et al. |
| 2011/0313383 A1 | 12/2011 | Hofstetter et al. |
| 2015/0275404 A1 | 10/2015 | Erlandsson et al. |

FOREIGN PATENT DOCUMENTS

| | | |
|---|---|---|
| JP | 2000-265341 A | 9/2000 |
| JP | 2001-55633 A | 2/2001 |
| JP | 2001-198154 A | 7/2001 |
| JP | 2003-159528 A | 6/2003 |
| JP | 2008-115476 A | 5/2008 |
| KR | 10-0882120 B1 | 2/2009 |
| RU | 2426579 C2 | 8/2011 |
| WO | WO-01/37888 A1 | 5/2001 |
| WO | WO-2013/141450 A1 | 9/2013 |
| WO | WO-2014/200394 A1 | 12/2014 |
| WO | WO-2016/032055 A1 | 3/2016 |
| WO | WO-2018/054455 A1 | 3/2018 |

OTHER PUBLICATIONS

Russian Decision to Grant dated May 27, 2020 issued in Russian patent application No. 2018122205 (5 pages) and its English-language translation thereof (5 pages).
Third Office Action dated May 25, 2021, by the Chinese Patent Office in corresponding Chinese Patent Application Mo 201580085743.6, and an English Translation of the Office Action. (7 pages).

* cited by examiner

FIBROUS STRUCTURE EXHIBITING AN ANTIMICROBIAL EFFECT

CROSS-REFERENCE TO PRIOR APPLICATION

This application is a § 371 National Stage Application of PCT International Application No. PCT/SE2015/051251 filed Nov. 20, 2015, which is incorporated herein in its entirety.

TECHNICAL FIELD

The present disclosure relates to a fibrous structure.

BACKGROUND

It is known in the art to make fibrous structures for use as wipes for object wiping such as counter tops, sinks, stoves etcetera. An important property for wipes is the absorption capacity, that the wipe is capable of picking up the moisture that is required. Another important property is absorption time, i.e. the length of time a spot has to be wiped or the number of times the same spot will have to be wiped to pick up the moisture needed.

Wipes of the described type are often reused multiple times. An aspect that comes into play with reused wipes is bacterial growth on the wipes. This leads to bad hygiene and often odor problems. Thus, there is a need for wipes that have antimicrobial properties. Different additives have been used to give wipes antimicrobial properties, such as a polyhydroxybiguanide (PHMB). However, adding PHMB to a nonwoven material decreases the absorption capacity and related absorbency properties such as absorption time.

Thus, there is a need for a material exhibiting both good absorbency properties as well as having antimicrobial properties.

SUMMARY

In an embodiment, a fibrous structure exhibits an absorbency time of equal to or less than 1.5 s and exhibiting an antimicrobial effect.

In an embodiment, a fibrous structure exhibits an absorbency of at least 5 g/g.

In an embodiment, a fibrous structure comprises zinc, silver or titanium oxide.

In an embodiment, a fibrous structure material comprises zinc oxide.

In an embodiment, a fibrous structure material comprises zinc oxide containing fibers in an amount of at least 5 wt % of the fibrous structure.

In an embodiment, a fibrous structure material includes zinc oxide present as a powder.

In an embodiment, a fibrous structure material includes zinc oxide present as part of the fibers.

In an embodiment, a fibrous structure material includes short fibers including natural or synthetic fibers.

In an embodiment, a fibrous structure material includes continuous filaments.

In an embodiment, a fibrous structure material is hydroentangled.

In an embodiment, a fibrous structure material has an antimicrobial effect corresponding to a logarithmic reduction of at least 2 units as determined by AATCC 100 for *S. Aureus* (ATCC 6538).

DETAILED DESCRIPTION OF PARTICULAR EMBODIMENTS

The absorbent material includes a mixture of continuous spunlaid filaments and short fibers including natural fibers and/or staple fibers. These different types of fibers as well as other details are defined as follows.

Continuous Filaments

Filaments are fibers that in proportion to their diameter are very long, in principle endless. They can be produced by melting and extruding a thermoplastic polymer through fine nozzles, thereafter the polymer will be cooled, for example by the action of an air flow blown at and along the polymer streams, and solidified into strands that can be treated by drawing, stretching or crimping. Chemicals for additional functions can be added to the surface.

Filaments can also be produced by chemical reaction of a solution of fiber-forming reactants entering a reagence medium, e g by spinning of viscose fibers from a cellulose xanthate solution into sulphuric acid.

Melt blown filaments are produced by extruding molten thermoplastic polymer through fine nozzles in very fine streams and directing converging air flows towards the polymers streams so that they are drawn out into continuous filaments with a very small diameter. Production of melt blown is e.g., described in U.S. Pat. No. 3,849,241 or 4,048,364. The fibers can be microfibers or macrofibers depending on their dimensions. Microfibers have a diameter of up to 20 µm, for example 2-12 µm. Macrofibers have a diameter of over 20 µm, for example 20-100 µm.

Spun bond filaments are produced in a similar way, but the air flows are cooler and the stretching of the filaments is done by air to get an appropriate diameter. The fiber diameter is usually above 10 for example 10-100 µm. Production of spun bond is e g described in U.S. Pat. No. 4,813,864 or 5,545,371.

Spun bond and melt blown filaments are as a group called spun laid filaments, meaning that they are directly, in situ, laid down on a moving surface to form a web that further on in the process is bonded. Controlling the 'melt flow index' by choice of polymers and temperature profile is an essential part of controlling the extruding and thereby the filament formation. The spun bond filaments normally are stronger and more even.

Tow is another source of filaments, which normally is a precursor in the production of staple fibers, but also is sold and used as a product of its own. In the same way as with spun laid fibers, fine polymer streams are drawn out and stretched, but instead of being laid down on a moving surface to form a web, they are kept in a bundle to finalize drawing and stretching. When staple fibers are produced, this bundle of filaments is then treated with spin finish chemicals, normally crimped and then fed into a cutting stage where a wheel with knives will cut the filaments into distinct fiber lengths that are packed into bales to be shipped and used as staple fibers. When tow is produced, the filament bundles are packed, with or without spin finish chemicals, into bales or boxes.

Figure 1:
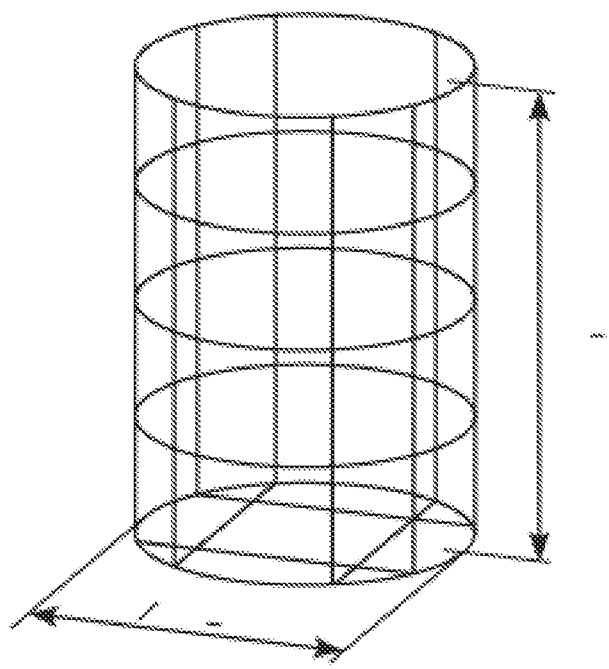
FIG. 1 is a schematic view of an exemplary steel wire basket used in the water absorption time and capacity test.

Any thermoplastic polymer that has enough coherent properties to let itself be drawn out in this way in the molten state, can in principle be used for producing melt blown or spun bond fibers. Examples of useful polymers are polyolefins, such as polypropylene and polypropylene, or polyesters, such as polylactides and polyethyleneterephtalate or polybutyleneterephtalate, or polyamides. Copolymers of these polymers may of course also be used, as well as natural polymers with thermoplastic properties.

Natural Fibers

There are many types of natural fibers that can be used, especially those that have a capacity to absorb water and tendency to help in creating a coherent sheet. Among the natural fibers possible to use there are primarily the cellulosic fibers such as seed hair fibers, e g cotton, kapok, and milkweed; leaf fibers e.g., sisal, abaca, pineapple, and New Zealand hemp; or bast fibers e g flax, hemp, jute, kenaf, and pulp.

Wood pulp fibers are especially well suited to use, and both softwood fibers and hardwood fibers are suitable, and also recycled fibers can be used.

The pulp fiber lengths will vary from around 3 mm for softwood fibers and around 1.2 mm for hardwood fibers and a mix of these lengths, and even shorter, for recycled fibers.

Staple Fibers

The staple fibers used can be produced from the same substances and by the same processes as the filaments discussed above. Other usable staple fibers are those made from man-made cellulose such as rayon or lyocell.

They can be treated with spin finish and crimped, but this is not necessary for the type of processes used to produce the material described in embodiments of the present invention. Spin finish and crimp is normally added to ease the handling of the fibers in a dry process, e.g. a card, and/or to give certain properties, e.g. hydrophilicity, to a material consisting only of these fibers, e.g. a nonwoven top sheet for a diaper.

The cutting of the fiber bundle normally is done to result in a single cut length, which can be altered by varying the distances between the knives of the cutting wheel. Depending on the planned use different fiber lengths are used, between 2-18 mm are known to be used.

For hydroentangled materials made by traditional wet laid technology, the strength of the material and its properties like surface abrasion resistance are increased as a function of the fiber length (for the same thickness and polymer of the fiber).

When continuous filaments are used together with staple fibers and pulp or just pulp, the strength of the material will mostly come from the filaments.

Antimicrobial Agents

It has surprisingly been shown that the addition of zinc oxide to nonwoven wipes gives the nonwoven material an antimicrobial property while not lowering the absorbency properties of the material. The zinc oxide may be added as a powder to the material or added to the nonwoven material as part of the fibers.

Process

One general example of a method for producing the absorbent material according to embodiments of the present invention includes the steps of:

Providing an endless forming fabric, where the continuous filaments can be laid down, and excess air be sucked off through the forming fabric, to form the precursor of a web, advancing the forming fabric with the continuous filaments to a wet laying stage, where a slurry including a mixture of short fibers including natural fibers and/or staple fibers is wet laid on and partly into the precursor web of continuous filaments, and excess water is drained off through the forming fabric, advancing the forming fabric with the filaments and fiber mixture to a hydro entangling stage, where the filaments and fibers are mixed intimately together and bonded into an absorbent material by the action of many thin jets of high-pressure water impinging on the fibers to mix and entangle them with each other, and entangling water is drained off through the forming fabric, advancing the forming fabric to a drying stage (not shown) where the absorbent material is dried, and further advancing the absorbent material to stages for embossing, rolling, cutting, packing, etc.

The continuous filaments made from extruded molten thermoplastic pellets may be laid down directly on a forming fabric where they are allowed to form an un-bonded web structure in which the filaments can move relatively freely from each other. This is achieved, for example, by making the distance between the nozzles and the forming fabric relatively large, so that the filaments are allowed to cool down before they land on the forming fabric, at which lower temperature their stickiness is largely reduced. Alternatively, cooling of the filaments before they are laid on the forming fabric is achieved in some other way, e.g., by means of using multiple air sources where air is used to cool the filaments when they have been drawn out or stretched to the desired degree.

The air used for cooling, drawing and stretching the filaments is sucked through the forming fabric, to let the filaments follow the air flow into the meshes of the forming fabric to be stayed there. A good vacuum might be needed to suck off the air.

The pulp and/or staple fibers are slurried in conventional way, either mixed together or first separately slurried and then mixed, and conventional papermaking additives such as wet and/or dry strength agents, retention aids, dispersing agents, are added, to produce a well-mixed slurry of short fibers in water.

This mixture is pumped out through a wet-laying headbox onto the moving forming fabric where it is laid down on the un-bonded precursor filament web with its freely moving filaments. The short fibers will stay on the forming fabric and the filaments. Some of the fibers will enter between the filaments, but the vast majority of them will stay on top of the filament web. The excess water is sucked through the web of filaments laid on the forming fabric and down through the forming fabric, by means of suction boxes arranged under the forming fabric.

Hydro Entangling

The fibrous web of continuous filaments and staple fibers and pulp is hydroentangled while it is still supported by the forming fabric and is intensely mixed and bonded into a composite nonwoven material. An instructive description of the hydro entangling process is given in CA Patent No. 841 938.

In the hydroentangling stage, the different fiber types will be entangled and a composite nonwoven material is obtained in which all fiber types are substantially homogeneously mixed and integrated with each other. The fine mobile spun laid filaments are twisted around and entangled with themselves and the other fibers which give a material with a very high strength. The energy supply needed for the hydro entangling is relatively low, i.e. the material is easy to entangle. The energy supply at the hydro entangling is appropriately in the interval 50-500 kWh/ton.

The pulp fibers are irregular, flat, twisted and curly and gets pliable when wet. These properties will let them fairly easily be mixed and entangled into and also stuck in a web of filaments, and/or longer staple fibers. Thus, pulp can be used with a filament web that is pre-bonded, even a pre-bonded web that can be treated as a normal web by rolling and unrolling operations, even if it still does not have the final strength to its use as a wiping material.

The entangling stage can include several transverse bars with rows of nozzles from which very fine water jets under very high pressure are directed against the fibrous web to provide an entangling of the fibers. The water jet pressure can then be adapted to have a certain pressure profile with different pressures in the different rows of nozzles.

Alternatively, the fibrous web can before hydro entangling be transferred to a second entangling fabric. In this case, the web can also prior to the transfer, be hydroentangled by a first hydro entangling station with one or more bars with rows of nozzles.

Drying Etc.

The hydro entangled wet web is then dried, which can be done on conventional web drying equipment, for example of the types used for tissue drying, such as through-air drying or Yankee drying. The material is after drying normally wound into mother rolls before converting. The material is then converted in known ways to suitable formats and packed. The structure of the material can be changed by further processing such as micro creping, hot calandering, etc. To the material can also be added different additives such as wet strength agents, binder chemicals, latexes, debonders, etc. The structure of the material can now be changed by the embossing described.

Composite Nonwoven Material

A composite nonwoven can be produced with a total basis weight of 40-120 g/m$^2$.

The unbonded filaments will improve the mixing-in of the short fibers, such that even a short fiber will have enough entangled bonding points to keep it securely in the web. The short fibers will result in an improved material as they have more fiber ends per gram fiber and are easier to move in the Z-direction (perpendicular to web plane). More fiber ends will project from the surface of the web, thus enhancing the textile feeling. The secure bonding will result in very good resistance to abrasion. However, the greatest effect of a soft feel is the embossing process.

Wet Strength Agent

In particular embodiments, the wet strength agent is a cationic polymer containing cationic groups, such as positively charged quaternary nitrogen atoms. The wet strength agent can be selected from, but is not limited to, urea-formaldehyde resins, melamine-formaldehyde resins, polyvinylamine, polyureide-formaldehyde resins, glyoxal-acrylamide resins and cationic materials obtained by the reaction of polyalkylene polyamines with polysaccharides such as starch and various natural gums, as well as 3-hydroxyazetidinium ion-containing resins, which are obtained by reacting nitrogen-containing polymers with epichlorohydrine. The above materials are mentioned in U.S. Pat. No. 3,998,690 where also references for their disclosure are found.

Embossing

A well-known technique to increase the thickness of a paper product is to emboss the paper web. Any embossing can lead to embossed elements all having the same height or to embossing elements having different heights. An embossing process may be carried out in the nip between an embossing roll and an anvil roll.

The embossing roll is formed of a hard material, usually metal, especially steel, but there are also known embossing rolls made of hard rubber or hard plastics materials. The embossing roll can have protrusions on its circumferential surface leading to so-called embossed depressions in the web or it can have depressions in its circumferential surface leading to so-called embossed protrusions in the web.

Anvil rolls may be softer than the corresponding embossing roll and may be formed of rubber, such as natural rubber, or plastic materials, paper or steel. However, structured anvil rolls, especially rolls made of paper, rubber or plastics materials or steel are also known. Said smooth backing roll may be a steel roll or a rubber roll, said rubber roll having a hardness between 50 and 90 shore according to ASTM D2240. The hardness of the rubber chosen depends on the pressure applied and is between 50 and 95 Shore A. In particular embodiments, the hardness has a value of about 45 to 60 Shore A. Typically, the embossing works much better with lower values on hardness in order to get a three dimensional in the structure and a deep embossing, typically 55 Shore A has been used. The combination of a high embossing structure together with a lower value of the hardness makes it possible to achieve the impressed stable embossing. It is also good that the material web can be pushed and pressed down into the rubber such that the web is deformed.

All above described methods have the following common features: the first embossing roll is formed of a hard material, usually metal, especially steel, but there are also known embossing rolls made of hard rubber or hard plastics materials. The embossing rolls can be a male roll having individual protrusions. Alternatively, the embossing roll can be a female roll with individual embossing depressions. Typical depths of embossing patterns are between 0.8 mm and 1.4 mm.

Another well-known embossing technique includes a steel embossing roll and a corresponding anvil steel roll (so-called Union embossing). The surfaces of these rolls are being formed in such a manner that deformation of the web is achieved within one single embossing step.

An example of the embossing is that it is made with a depth of the embossing protrusions of about 2.5 mm against an anvil roll of a hardness of 55 Shore A. The repeat height is 13.3 mm and the repeat width is 5.7 mm and the embossing figure is an oval of 3.8×2.2 mm and a depth of 2.5 mm. Every other row of oval embossments is aligned and the rows in between are centrally offset in the middle and in turn also aligned by every other row. The oval has its length in the machine direction of the web material. The embossed area is about 10 percent but can optionally be anything from 3 to 20 or even 50%, for example between 10 and 30%. In fact, as the embossing is not destructive, the embossed area can be chosen rather freely.

The softness of the anvil roll together with the height of the embossing protrusion is a combination that has carefully been elaborated and is important in order to get the three dimensional structure in the material web. Further, the amount of embossing spots in an area can also influence. In the above mentioned example, there are 2.9 spots per cm$^2$.

Embodiments of the invention are further described in the examples below. The invention may however be embodied in many different forms and should not be construed as limited to the embodiments set forth in the description thereto.

Test Procedures:

ABSORPTION CAPACITY, DIN 54 540 (modified)

(a) Purpose and Field of Application

To decide a material's ability to hold fluid. Used for both tissue and nonwoven.

(b) Definition (c) Principle

A weighted test sample is soaked in water during 60 seconds, then hung to drip of under 120 seconds, and weighted thereafter.

(d) Apparatus
Stop-watch
Scale with an accuracy of ±0.01 g
Beaker, 3000 ml, low model with a flat bottom
Paper clamps which fixate the test sample in 3 spots (e) Sample Preparation
Material consumption: Approx. 0.1 m² distributed over the material.
Number of samples: 5 pieces
Preparation: The samples are punched into squares in both MD and CD with the side 100±0.5 mm.
Conditioning: 23° C., 50% RH in at least 4 h
De-ionized water, temperature of 23 degrees
The water shall be changed after each test batch (5 samples)

(f) Procedure
A material which is made of several layers should be tested as a whole product. The sample is weighed to an accuracy of 0.01 g. Thereafter, it is attached with the paper clip intended for DIN 54 540, so that the sample is attached in three points. The machine direction of the sample should be vertical when hung. A bowl with a flat bottom is filled with liquid and the sample is submerged for 60±3 seconds to then be hung up to drip for 120±3 seconds. It is important that the sample hangs freely and straight during the dewatering. After 120 seconds, the sample is released from the clip and re-weighed with an accuracy of 0.01 g.

(g) Calculation and Expression of Results
The weight of the sample before and after wetting is measured, the absorption is calculated according to the below formula and a mean value for the absorption is calculated for the samples.

$$\text{Absorption} = \frac{m_v - m_t}{m_t} [g/g]$$

$m_v$=the mass of the wet sample [g]
$m_t$=the mass of the dry sample [g]
Report the mean value with the accuracy of one decimal.

(h) Reference
Original method: DIN 54 540, part 4
Deflection from the reference method:
Soaking of the sample is different from the original method, where the sample is put horizontally, but in this case is hung vertically.

WATER ABSORPTION TIME AND CAPACITY, ISO 12625-8 (basket absorption)

(i) Purpose and field of application
The purpose is to determine the water absorption time and the water absorption capacity of tissue paper and finished tissue products using the basket immersion method manually.

(j) Definition
Ply Independently formed unit of unlaminated tissue, like that made directly from a tissue machine.
Sheet Unit of a laminated or unlaminated tissue, like that present in the finished tissue product.
Water absorption The time it takes for a test piece to become completely
time wetted [s]
Water absorption Amount of water the test piece is able to absorb
capacity [g water/g material in test piece]

(k) Principle
A test piece of defined width and total mass is placed in a cylindrical basket which is dropped from a defined height over a water surface. The time is measured from when the basket is dropped until the test piece has been fully wetted and the results serve as water absorption time. The amount of absorbed water is determined from the dry and wet weight of the test piece.

Figure 2:
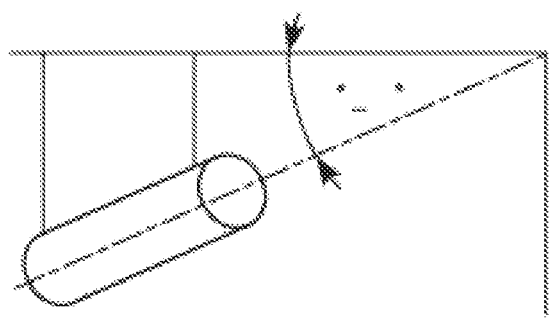
FIG. 2 is an exemplary view of the steel wire basket hanging at an angle of about 30°.

(l) Equipment
Steel wired basket, weight 3.0±0.1 g, diameter 50±1 mm, height 80±1 mm (see FIG. 1)
Water container, volume at least 3 liters (minimum depth of water 100 mm)
Balance with an accuracy of 0.001 g
Draining equipment, so that the basket can hang at a 30±3° angle with the horizontal (see FIG. 2)
Timer(s) with accuracy of 0.1 s
Deionized water, conductivity ≤0.25 mS/m at 25° C., in accordance with ISO 14487

(m) Sample Preparation
Prepare the test pieces by cutting the material in machine direction to a width of 76±1 mm and enough length so that the total mass of each test piece is 5.0±0.2 g. If more than one sheet is needed, all sheets should have the top side up. If several sheets are cut at once, separate them before testing. Select the test pieces randomly from the entire test specimen. Cut enough material for 5 observations for an official LAB test reports.

(i) Conditioning
Condition the prepared samples for minimum 2 hours at 23° C. and 50% rel. humidity. Note: in ISO 14187 it is stated that a conditioning time of 4 h is sufficient, however, prepared tissue samples have been found to condition within 2 h. Not mandatory for production control, however a stable and controlled climate is necessary.

(n) Procedure Record the Mass of the Test Piece to the Nearest 0.01 g. Dry Test Piece Mass=$m_0$
Record the mass of the basket to the nearest 0.01 g. Basket mass=$m_b$
Roll the test piece so that they fit in the basket without folding it and place it in the basket (Use of a pen can help). It should be loosely packed in the basket.
Position the basket with test piece at a height of 25±5 mm from the water surface, keeping it horizontal and parallel to the water surface.
Release the basket into the water and start the timer at the same time.
Stop the timer when the test piece is completely immersed in the water even if it has not yet sunk to the bottom. Record the wetting time to the nearest 0.1 s.
Allow the basket to remain in the water for 30±1 s, and then take it out in a horizontal position.
Hang the basket at 30±3° angle and let it drain for 60±1 s.
Carefully place the basket on the scale and record the mass of the basket with the wetted sample to the nearest 0.01 g. Basket mass+wet sample mass=$m_n$
Repeat for the remaining test pieces. Carefully wipe down the basket between test pieces. It is recommended to change the water after five tests.

(o) Calculation and Expression of Results
Calculate the water absorption capacity, $W_a$:

$$W_a = \frac{m_n - m_0 - m_b}{m_0}$$

where $m_n$=basket mass+wet sample mass [g]
$m_0$=dry test piece mass [g]
$m_b$=basket mass [g]

Calculate the average value and standard deviation of the readings for both water absorption time and water absorption capacity.

(i) Results Reporting

Water absorption time is reported in seconds [s] to the nearest 0.1 s.

Water absorption capacity is reported in grams water per gram test piece [g/g] to the nearest 0.1 g/g.

All deviations from this method must be noted in the report.

(ii) Typical Standard Deviations (Relative Standard Deviation; Coefficient of Variation):

10% RSD for water absorption time.

3% RSD for water absorption capacity.

(p) Validation

A production site or laboratory is considered qualified when passing a t-test on 95% confidence level compared with an R&D-laboratory or another qualified laboratory, and regular re-qualifications are made with comparative measurements among sites.

(q) Reference

ISO 12625-8:2011 Water-absorption time and water-absorption capacity, basket-immersion test method
ISO 14487 Pulps—Standard water for physical testing
ISO 187—Standard atmosphere for conditioning and testing tissue

EXAMPLES

Sample 1

This is a reference sample of a hydroentangled spunlaced nonwoven material (70% pulp fibers, 25 wt % polylactide filaments, 5 wt % polylactide staple fibers (1.7 dtex, 6 mm length)). The material is 630 µm thick and has a basis weight of 66 g/m². Wet strength agent is added to the material in an amount of 0.3 wt (Kymene GHP 020 from Solenis).

Sample 2

Carded, apertured spun lace nonwoven material (70 wt % viscose fibers, 30 wt % polyethyleneterephtalate fibers). Treated with microban antibacterial treatment. The thickness of the material is 732 µm and basis weight is 72.3 g/m².

Sample 3

Carded, apertured spunlace nonwoven (70 wt % viscose fibers, 30 wt % polyethyleneterephtalate fibers). The thickness of the material is 596 µm and basis weight is 65.4 g/m².

Sample 4

A hydroentangled spunlaced nonwoven material (70% pulp fibers, 25 wt % polylactide filaments, 5 wt % viscose fibers containing zinc oxide (Smartcell Sensitive from Smartfibers)) (2.5 dtex, 10 mm length). Wet strength agent is added to the material in an amount of 0.3 wt %. Wet strength agent added to the material in an amount of 0.3 wt % (Kymene GHP 020 from Solenis). Thickness of the material is 608 µm and basis weight is 63.9 g/m².

Results Absorption

The results from the absorption tests are shown in table 1.

TABLE 1

| Sample | Absorption DIN 54 540 (g/g) | Absorption time (s) |
|---|---|---|
| 1 | 5.6 | 1.1 |
| 2 | 7.4 | 1.8 |
| 3 | 5.8 | 15.4 |
| 4 | 5.4 | 1.2 |

Microbiological Test (AATCC 100)

The antibacterial effect of a nonwoven wipe with ZnO was measured and compared to a reference nonwoven wipe.

The reference nonwoven wipe contained 25% PLA filament, 5% PLA Staple fibers and 70% pulp. It was compared to a material with 25% PLA filament, 5% Viscose containing ZnO (Smartcell Sensitive) 2.5 dtex 10 mm and 70% Pulp.

Test bacteria were *S. aureus* (ATCC 6538). An overnight culture was grown in Tryptone Soy Broth (TSB). It was diluted in saline (0.9%) to an approximate concentration of $10^6$ CFU/ml. (verified by cultivation, pour plate technique, on Tryptone Soy Agar (TSA)).

Small pieces of the two test materials were punched out (circular pieces with diameter 36 mm). A stack of the different materials were put in sterile petri dishes. The amount of material had been tested out in advance to be just enough to absorb 1 ml of fluid. In this case, 0.28 g of each material was used. 1 ml of the bacteria/saline blend was added to the stacks of material. Duplicates were tested from each of the two test materials. After a contact time of 6 hours (in 35° C.) the amount of bacteria in the stacks was counted. The whole stack of material was put in plastic bag together with 100 ml 0.9% NaCl, stomached during 1 minute and then counted by pour plate technique on TSA.

The logarithmic reduction was calculated and the Figure below shows the mean value of the logarithmic reduction for the two materials tested. It is important to always compare with a reference material without antibacterial agent since some bacteria always are trapped in a fibrous material.

| Nonwoven material | CFU/ml in liquid added to the material | CFU/ml after 6 hours incubation (35 C.) | Logarithmic reduction | Mean value from the duplicates |
|---|---|---|---|---|
| Sample 1, duplicate 1 | $1.16 \times 10^6$ | $9.80 \times 10^4$ | 1.07 | 1.04 |
| Sample 1, duplicate 2 | $1.16 \times 16^6$ | $1.15 \times 10^5$ | 1.00 | |
| Sample 4, duplicate 1 | $1.16 \times 10^6$ | $7.00 \times 10^3$ | 2.22 | 2.29 |
| Sample 4, duplicate 2 | $1.16 \times 10^6$ | $5.00 \times 10^3$ | 2.37 | |

The invention claimed is:

1. An absorbent nonwoven material having a fibrous structure comprising:
    a mixture of continuous spunlaid filaments and short fibers comprising natural fibers and/or staple fibers;
    the absorbent nonwoven material having an absorbency time of equal to or less than 1.5 s and exhibiting an antimicrobial effect;
    the absorbent nonwoven material being hydroentangled and having a total basis weight of 40-120 g/m₂, and wherein the absorbent nonwoven material comprises an antimicrobial agent in an amount of at least 5 wt % of the fibrous structure.

2. The absorbent nonwoven material according to claim 1, further exhibiting an absorbency of at least 5 g/g.

3. The absorbent nonwoven material according to claim 1, wherein the antimicrobial agent comprises zinc, silver or titanium oxide.

4. The absorbent nonwoven material according to claim 1, wherein the antimicrobial agent comprises zinc oxide.

5. The absorbent nonwoven material according to claim 1, wherein the antimicrobial agent comprises zinc oxide fibers.

6. The absorbent nonwoven material according to claim 4, wherein the zinc oxide is present as a powder.

7. The absorbent nonwoven material according to claim 4, wherein the zinc oxide is present as part of the fibers.

8. The absorbent nonwoven material according to claim 4, comprising short fibers, the short fibers comprising natural or synthetic fibers.

9. The absorbent nonwoven material according to claim 1, the fibrous structure comprising continuous filaments.

10. The absorbent nonwoven material according to claim 1, wherein the fibrous structure is hydroentangled.

11. The absorbent nonwoven material according to claim 1, wherein the fibrous structure has an antimicrobial effect corresponding to a logarithmic reduction of at least 2 units as determined by AATCC 100 for *S. aureus* (ATCC 6538).

12. The absorbent nonwoven material according to claim 1, wherein the absorbency time is calculated in accordance with the ISO 12625-8 test.

13. The absorbent nonwoven material according to claim 2, wherein the absorbency is calculated in accordance with the ISO 12625-8 test.

14. The absorbent nonwoven material according to claim 12, wherein the absorbency is calculated in accordance with the ISO 12625-8 test.

* * * * *